United States Patent [19]

Kesling

[11] Patent Number: 4,664,626
[45] Date of Patent: May 12, 1987

[54] SYSTEM FOR AUTOMATICALLY PREVENTING OVERTIPPING AND/OR OVERUPRIGHTING IN THE BEGG TECHNIQUE

[76] Inventor: Peter C. Kesling, 611 W. 250 S., LaPorte, Ind. 46350

[21] Appl. No.: 713,480

[22] Filed: Mar. 19, 1985

[51] Int. Cl.[4] .............................................. A61C 3/00
[52] U.S. Cl. ........................................ 433/16; 433/8; 433/14; 433/18
[58] Field of Search ................. 433/8, 9, 10, 11, 12, 433/13, 14, 15, 16, 18

[56] References Cited

U.S. PATENT DOCUMENTS

| | | | |
|---|---|---|---|
| 2,854,747 | 10/1958 | Lewis | 433/8 |
| 2,926,422 | 3/1960 | Wallshein | 433/8 |
| 3,085,335 | 4/1963 | Kesling | 433/14 |
| 3,085,336 | 4/1963 | Kesling | 433/14 |
| 3,178,821 | 4/1965 | Kesling | 433/14 |
| 3,307,261 | 3/1967 | Steiner | 433/15 |
| 3,445,933 | 5/1969 | Kesling | 433/14 |
| 3,793,730 | 2/1974 | Begg et al. | 433/14 |
| 4,242,085 | 12/1980 | Wallshein | 433/16 |
| 4,531,911 | 7/1985 | Creekmore | 433/8 |

OTHER PUBLICATIONS

Angle, "Special Mechanism for the Treatment of Deciduous and Mixed Dentures", Dental Cosmos, vol. LXVI, May, 1924, pp. 539, 549.
Angle, "The Latest and Best in Orthodontic Mechanism", Dental Cosmos, vol. LXXI, Feb., 1929, pp. 164–169.
Begg, "Stone Age Man's Dentition", AJO, vol. 40, Nos. 4–7, 1954, pp. 298–312, 373–383, 462–475, 517–531.
Begg, "Differential Force in Orthodontic Treatment", AJO, vol. 42, No. 7, pp. 481–510.
Unitek Catalog 116, 1973, p. 41.

Primary Examiner—John J. Wilson
Attorney, Agent, or Firm—Lloyd L. Zickert

[57] ABSTRACT

A Begg bracket for controlling the tipping and/or uprighting movements of a tooth on which the bracket is mounted which includes mesial and/or distal archwire stops at the mesial and/or distal sides of the archwire slot to limit the mesial and/or distal tipping and/or uprighting of a tooth to predetermined amounts where mesial or distal tipping force is applied to the crown of the tooth by archwires and/or elastic auxiliaries to principally move the crown, and mesial or distal uprighting forces are applied to a tooth to principally move the root of the tooth.

10 Claims, 11 Drawing Figures

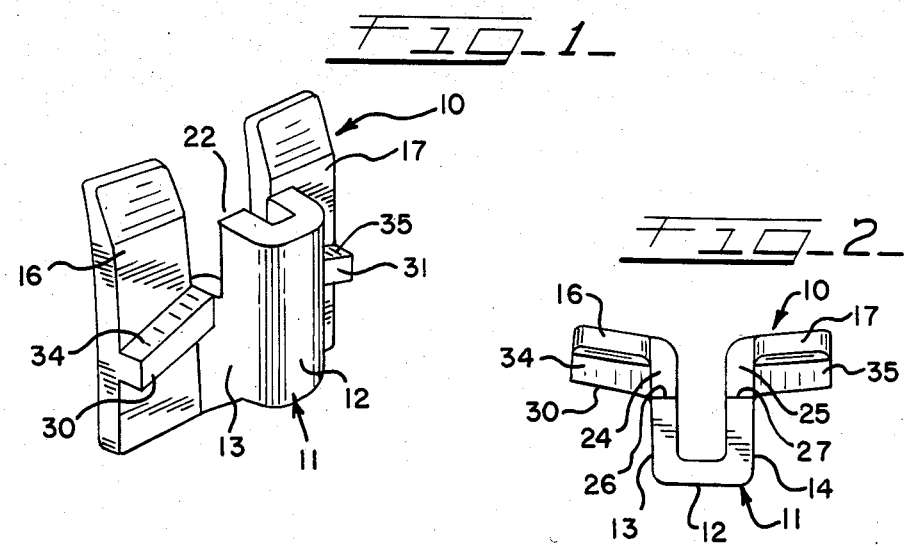
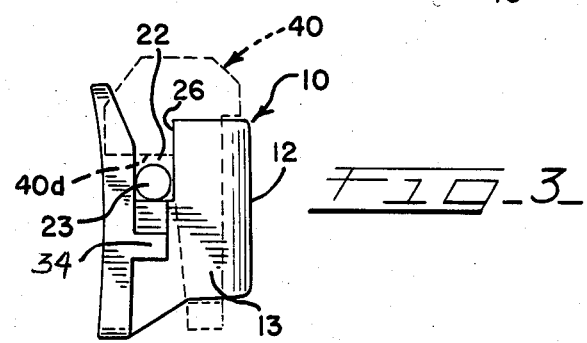
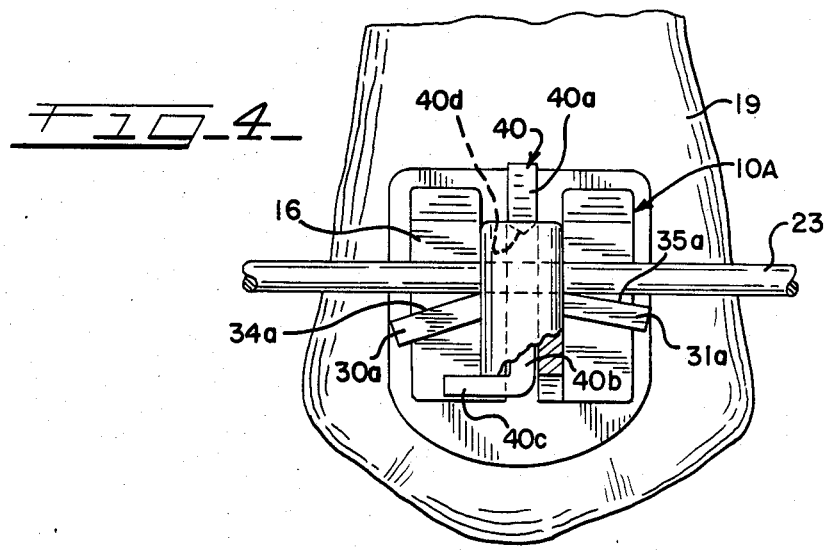

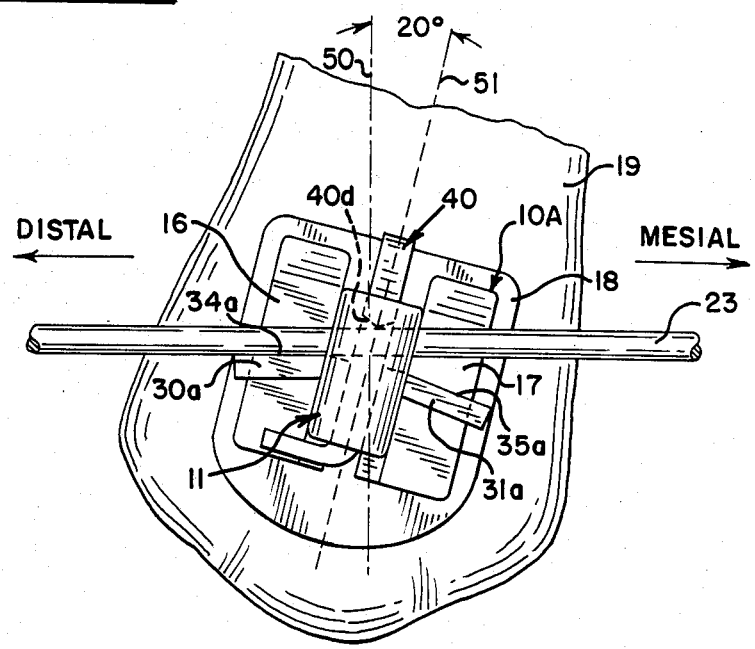
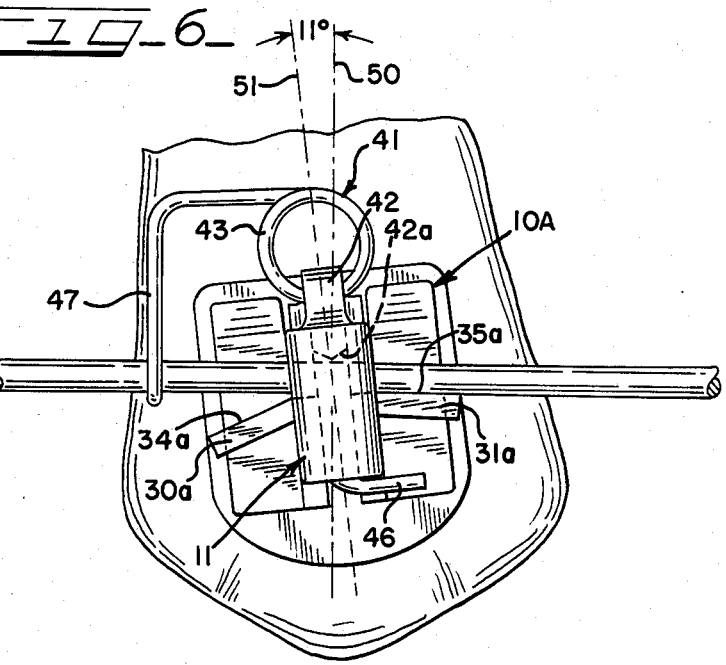

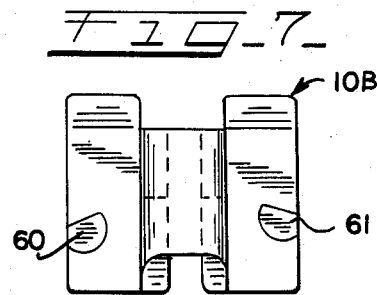
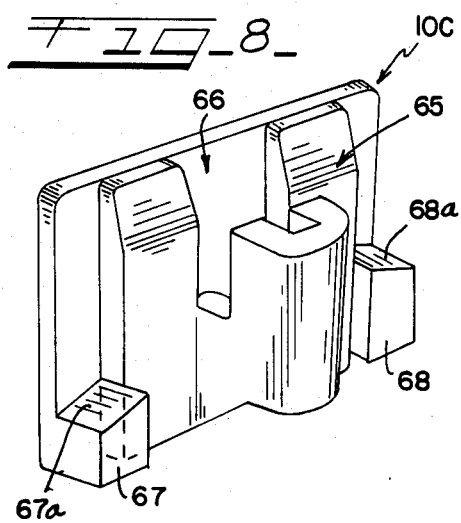
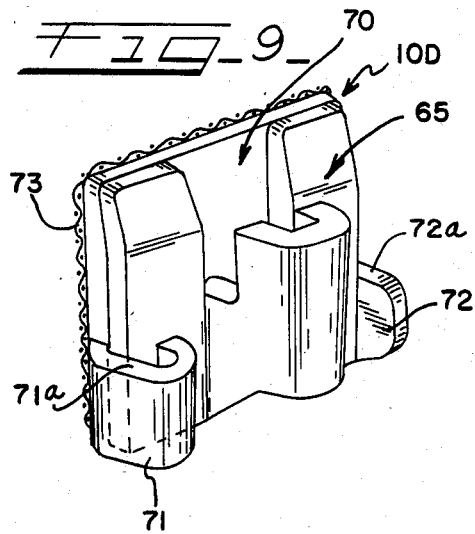
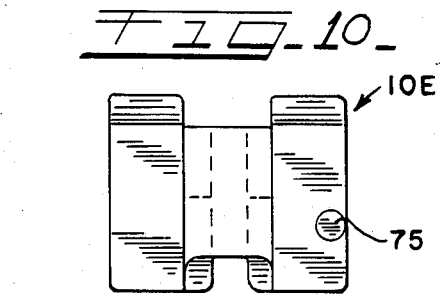
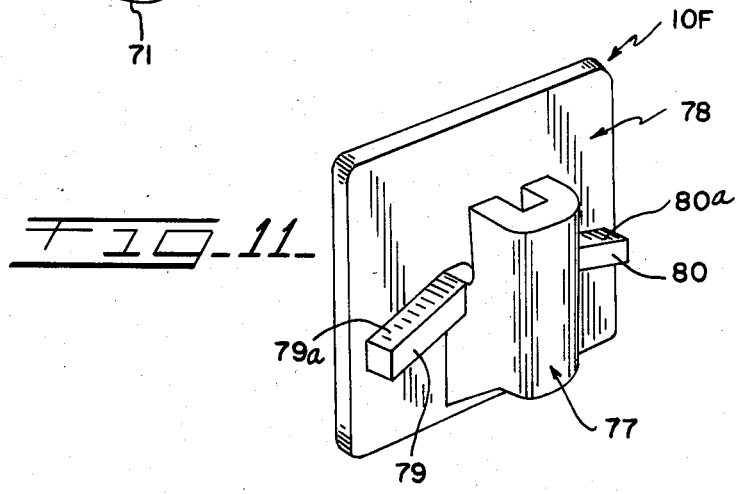

SYSTEM FOR AUTOMATICALLY PREVENTING OVERTIPPING AND/OR OVERUPRIGHTING IN THE BEGG TECHNIQUE

DESCRIPTION

This invention relates in general to a system for preventing overtipping and overuprighting in the Begg technique, and more particularly to means for a Begg bracket to limit tipping and/or uprighting tooth movement between visits to the orthodontist.

The terms "tipping" and "uprighting" relate to movements of teeth caused by the application of selected forces. Generally, "tipping" refers to either mesial or distal movement of the crown of a tooth, while "uprighting" refers to either mesial or distal of the root of a tooth. Thus, crown movement will be referred to as tipping, while root movement will be referred to as uprighting. The use of "and/or" herein is intended to cover three alternatives. For example, "mesial and/or distal archwire stops" means mesial and distal archwire stops or mesial archwire stops or distal archwire stops.

BACKGROUND OF THE INVENTION

Heretofore, it has been well known to effect tipping and/or uprighting movements to a tooth in the Begg technique by applying horizontal force directly to the crown or uprighting force between a Begg bracket mounted on a tooth and an archwire connected to the bracket. The most common bracket employed for this technique is the type similar to the Model 256 bracket manufactured and sold by TP Laboratories, Inc. of LaPorte, Ind. This bracket includes a vertically oriented body having an occlusogingivally extending opening for receiving a lock pin, a spring pin, or other appliances, attaching flanges at the mesial and distal sides of the body and which extend somewhat above and below the upper and lower ends of the body, and a mesiodistally extending archwire slot, which when the bracket is mounted on the tooth in a given orientation is usually disposed at the gingivolingual corner of the body extending vertically and opening gingivally. Another form of this bracket differs in that the flanges are tapered and then only extend from the body below the archwire slot, but those flanges were purposely designed to never engage the archwire and therefore would be of no practical value as stops. Normally, the bracket is mounted in this manner with the archwire slot opening gingivally, but it could be mounted so that the slot opens occlusally. However, this bracket does not have any practical means for predetermining the limits of either tipping or uprighting movements which are produced by applying forces to the crown or root of a tooth to cause mesial or distal tipping of the clinical crowns or mesial or distal uprighting of the roots. Accordingly, once an appliance system has been mounted in a patient's mouth and a tipping action is commenced, such as by contact of a proximate tooth being moved or by the use of elastics or the like, the tipping action will continue until the force is expended or neutralized at a subsequent appointment, or the tooth has been placed in an undesired and possibly detrimental inclination. Unexpected over-tipping can be caused by a longer time span between appliance adjustments than planned or by the inadvertent application of excessive forces by the orthodontist or patient. When overtipping is encountered, treatment time is lengthened and/or the quality of the result can be lessened.

Uprighting of a root is usually achieved with a suitable uprighting spring appliance. Inasmuch as it is normal for expeditious uprighting that the activation of the spring would upright a tooth beyond the desired position before the spring force is expended, uprighting movement heretofore has been generally stopped by removal of the spring at a subsequent visit to the orthodontist. Such control is satisfactory if the patient returns for treatment at the next scheduled appointment, the interval between appointments is not excessive, and the tooth does not upright more rapidly than expected. Should the patient miss the next appointment or the tooth respond quickly, excessive and undesired root uprighting may take place which then must be corrected through further treatment.

Spring Pin appliances are commonly used on Begg brackets to provide uprighting movements while locking the archwire to the bracket. "Spring Pin" is a registered trademark of TP Laboratories, Inc. for an appliance that not only locks an archwire to a bracket but also produces mesial-distal uprighting movement between the bracket and the archwire. More detailed operation of the appliance may be found in U.S. Pat. No. 3,793,730, including disclosure of an arm in FIG. 2 to limit uprighting, but to date it has not proved practical to commercially provide Spring Pin appliances with this arm. Therefore, practitioners of the Begg technique sometimes run into difficulties and experience overuprighting movements, especially when the time interval between patient visits is prolonged. For example, if a patient becomes hospitalized or otherwise disposed so that the patient is unable to make the next scheduled appointment and one or more teeth are undergoing uprighting action, overuprighting movements are encountered which require rectification. Such delays can extend the orthodontic treatment and cause severe problems for both patient and orthodontist.

Excessive tipping and/or uprighting extends treatment time and delays reaching the desired end result. These problems have been considered by many orthodontists to be serious deficiencies in the Begg technique and have deterred them from using the technique.

While there have been brackets usable in the Begg technique which include wide archwire slot bases or archwire supporting bars spaced from the archwire slot, such as shown in U.S. Pat. No. 3,085,335, the purpose of these elements has been to prevent tipping. It has also been proposed by Dr. P. R. Begg to solder horizontal spurs to bands to accomplish mesial and distal bodily tooth movements and to prevent mesial and distal tipping. Dr. Angle, many years ago, proposed adding staples to bands for tying ligature wires to the archwire to effect desired inclined tooth movements.

In recent years there has been considerable development of brackets intended to produce more accurate and satisfactory orthodontic treatment. This has been particularly evident in the edgewise technique which utilizes a rectangular or square wire received in a rectangular slot. Particularly, an offshoot of the edgewise technique is the straight-wire technique which compensates for malpositioned teeth in the structure of the brackets as opposed to applying bends in the wire. However, there have not been any developments of products in the light-wire or Begg technique parallel to those in the edgewise technique for obtaining such precise and accurate tooth inclinations throughout treatment, except for attempts to combine edgewise and light wire brackets as disclosed in the Universal bracket marketed by Unitek of Monrovia, Calif.

It has been well known that the edgewise technique has relied upon closely spaced patient visits for making adjustments in the system because it is designed to produce small amounts of movement between adjustments. It has also been known that periodic patient visits when using the Begg technique are usually spaced relatively far apart because the system contemplates greater tooth movements between adjustments.

In the edgewise technique, when it is desired to move a tooth along a jaw, the tooth is bodily moved along an archwire with a heavy force, often with the help of headgear, while in the Begg technique a tooth is generally moved by first tipping the crown mesially or distally, with a relatively light force, then holding the crown against horizontal movement and uprighting the root with an uprighting spring. A further objective of each technique is to orient the tooth in a predetermined inclined position. For example, many orthodontists believe the ideal inclination of an upper cuspid measured between the vertical axis of the mouth and the long axis of the clinical crown is about 11 degrees with the root tipped toward the distal.

One of the most common objections to the Begg technique, as above mentioned, is that it is difficult to control tooth movements. More particularly, orthodontists have expressed concern that tipping and uprighting movements are difficult to control because of the lack of predetermined restriction of such movements from the bracket through its relationship with the archwire.

SUMMARY OF THE INVENTION

The present invention obviates the above difficulties heretofore known in the Begg technique by freely permitting and yet accurately limiting tipping and uprighting movements to prevent such movements from exceeding a predetermined amount. Accordingly, the heretofore objectionable overtipping in the early stages and/or overuprighting in the final stage, associated with the Begg technique, is eliminated whether or not the scheduled time interval or forces between visits is exceeded. With the present invention, it is no longer necessary to rely on complete patient cooperation in making a scheduled visit or the orthodontist's subjective decision on the amount of force to apply to prevent overtipping or overuprighting action. Moreover, the present invention provides the orthodontist with a positive and automatic system that allows use of the Begg technique for obtaining the ideal and proper inclination for a specific tooth.

The system of the present invention may utilize a bracket that includes the conventional U-shape in cross section body defining an occlusogingivally extending pin opening with mesial and distal attaching flanges at the lingual side of the body for attaching the bracket to a bonding base or a band, or the bracket may be cast and have an attaching flange radiating along the back of the body. A notch in the body coacts with the attaching flanges to define a vertically opening horizontally extending archwire slot, the base of which is relatively narrow and parallel to the horizontal axis of the body. Tipping and/or uprighting control means are mounted on or an integral part of the labial surfaces of the attaching flanges or the sides of the body adjacent the archwire slot and consist of mesial and/or distal archwire stops. Each stop or control means includes a gingivally facing surface against which the archwire will engage when the desired tipping and/or uprighting movement has been accomplished. The archwire stops are located in relation to the base of the archwire slot to limit the mesial or distal tipping as well as the final desired upright inclination the archwire stop surfaces may be inclined downwardly from the opposite ends of the archwire slot at angles to the horizontal axis of the bracket body. For retraction movement, the distal stop controls crown tipping, and the mesial stop controls the root during uprighting. For protraction, the mesial stop controls crown tipping, while the distal stop controls root uprighting. The angle created between the long (vertical) axis of the clinical crown and the archwire by the root uprighting stop is equal to the desired angle of inclination for a specific tooth when the fixed appliances are removed, while the angle created by the crown tipping stop is dependent upon the amount of retraction or protraction movement desired for a particular tooth. Both depend upon the original malocclusion, treatment plan and goals for each patient, as determined by the orthodontist. In malocclusions requiring considerable retraction the angle established by the distal crown tipping stop is usually greater than that of the mesial or root uprighting stop which determines the final inclination of the tooth.

It is therefore an object of the present invention to provide a system for automatically limiting tipping and uprighting in the Begg technique.

Another object of the invention is to provide means for a Begg bracket to prevent overtipping and overuprighting.

A further object of the present invention is to provide a Begg bracket having means for limiting tipping and/or uprighting movements whether the movements are part of a retraction or protraction movement for a tooth or otherwise for only an uprighting movement.

It is a further object of the present invention to provide a Begg bracket having tipping and/or uprighting stops for limiting tooth movement and ultimate disposition of the long axis to a proper and desired inclination.

A still further object of the present invention is to provide a Begg bracket having a crown tipping stop on one side of the body and/or a root uprighting stop along the other side of the body for providing a positive and automatic system for obtaining desired tooth movements without solely relying on force values and/or patient cooperation to make scheduled visits thereby preventing objectionable overtipping and/or overuprighting.

Other objects, features and advantages of the invention will be apparent from the following detailed disclosure, taken in conjunction with the accompanying sheets of drawings, wherein like reference numerals refer to like parts, in which:

BRIEF DESCRIPTION OF THE DRAWINGS

FIG. 1 is a perspective view of the Begg bracket according to the invention;

FIG. 2 is a top plan view of the bracket of FIG. 1;

FIG. 3 is a side elevational view of the bracket of FIG. 1 and showing an archwire and safety lock pin in place;

FIG. 4 is a front elevational view of a modification of the bracket of the invention attached to a base and bonded to the upper right cuspid as it might occur at the beginning of treatment and fitted with a safety lock pin for locking an archwire to the bracket;

FIG. 5 is a view similar to FIG. 4, following the application of a suitable force, and illustrating the accomplished tipping movement of the tooth where the archwire is in abutting relation with the crown tipping stop on the distal side of the bracket and also illustrating the angle of tipping movement; and FIG. 6 is a view similar to FIG. 5, except a Spring Pin appliance is substituted for the lock pin to uprighting movement, and illustrating the uprighting of the root where the archwire is abutting against the uprighting stop on the mesial side of the bracket;

FIG. 7 is a front elevation of a further modification showing posts or tabs functioning as the stops at the mesial and distal sides of the bracket;

FIG. 8 is a perspective view of a further modification of the invention wherein a standard bracket is mounted onto a plate having archwire stops integrally formed wtih the plate and extending from the plate so that they coact with the bracket body to control mesial and/or distal tipping;

FIG. 9 is a perspective view of a further embodiment of the invention and similar to FIG. 8 except that a plate mounted on the back of a standard bracket is provided with bent archwire stops of two different types and which also may then have attached to the plate mesh for bonding the assembly to a tooth;

FIG. 10 is a front elevational view of a further embodiment of the invention and being similar to FIG. 7 except that an archwire stop is provided on only one of the flanges for controlling root uprighting; and FIG. 11 is a perspective view of a further embodiment of the invention illustrating a cast or molded bracket which includes an integral base radiating from the backside or lingual side of the bracket body.

DESCRIPTION OF THE INVENTION

Referring now to the drawings, and particularly to FIGS. 1 to 3, the Begg control bracket of the present invention is illustrated and generally designated by the numeral 10. The bracket generally includes a body 11 of U-shape cross section and having a front or labial or buccal wall 12 and opposed or mesial and distal walls 13 and 14 defining an occlusogingivally extending pin opening 15. Attaching flanges 16 and 17 are disposed at the lingual side of the body and extend mesial and distal of the body for suitable attachment to a bonding base or a band. Where the bracket may be molded or cast, it may then be directly bonded to a tooth. As seen in bracket 10A in FIGS. 4 to 6, the attaching flanges 16 and 17 of the bracket 10 are attached to a bonding base 18, which is in turn direct-bonded to a tooth 19.

The body 10 is notched at the gingivolingual corner to define a vertically opening horizontally extending archwire slot 22 for suitably receiving an archwire, as illustrated in FIGS. 4 to 6, wherein an archwire 23 is illustrated. The base of the slot 22 is defined by the surfaces 24 and 25 and which are normally in a horizontal plane extending perpendicular to the vertical axis of the bracket. The slot is additionally defined by the upstanding vertical surfaces 26 and 27 which are in substantially parallel relation to the attaching flanges 16 and 17 that complete the slot structure. The preceding elements of bracket 10 have been well known and have heretofore constituted the most widely used type bracket for the Begg or light-wire technique.

The bracket of the present invention differs from the well known Begg or light-wire bracket in that it includes control elements in the form of tipping and/or uprighting stops, which are located mesial and/or distal to the bracket body. These stops coact with the archwire retaining means to limit tipping or uprighting movements, and may take a variety of forms such as shown in the embodiments 10, 10A, 10B, 10C, 10D, 10E and 10F of FIGS. 1, 4, 7, 8, 9, 10 and 11. Archwire retaining means illustrated include a safety lock pin (FIGS. 3, 4 and 5) and a Spring Pin appliance (FIG. 6).

Archwire stop means in the embodiment of FIGS. 1 to 3 are designated 30 and 31. They are disposed on the attaching flanges 16 and 17 for controlling relative tipping and uprighting movement between the bracket and the archwire and may be integrally formed with the flanges, as shown in this embodiment, or suitably added to the flanges, as shown in the embodiment 10A of FIGS. 4 to 6. Since the open end of the archwire slot 22 is normally intended to face the gingival, the stop on the side of the body at the mesial is referred to as a mesial stop, while the stop on the side of the body at the distal will be considered the distal stop. Depending upon whether the bracket is mounted on the upper arch or the lower arch, the mesial and distal stops will be on one side or the other or on both sides of the body. It may be appreciated, as above mentioned, that the brackets may also be mounted with the slot opening occlusally.

For purposes of explaining the invention, the bracket 10 illustrated in FIGS. 1 to 3 will be considered to be one designed for a cuspid tooth of the upper arch on the right side of the mouth. Accordingly, the stop 30 is on the distal side and the stop 31 is on the mesial side. It will be understood that, as has been heretofore common with other techniques, brackets can be designed for specific teeth.

With the above in mind, the distal stop 30 includes a gingivally facing surface 34, while the mesial stop 31 includes a gingivally facing surface 35. As seen particularly in FIG. 3, the depth of the surface 34 is substantially equal to the depth of the archwire slot 22 or at least of sufficient depth to serve as a stop for the archwire received in the slot. Likewise, as particularly seen in FIG. 2, the mesial surface 35 is of the same depth as the distal surface 34. Further, the surfaces 34 and 35 are inclined or located downwardly or occlusally from the base of the archwire slot. In the embodiment of FIGS. 1 to 3, the surfaces are continuous from the body to the edge of the bracket, starting at the base of the slot and extending downwardly to the bracket edge seen particularly in FIGS. 1 and 2. Thus, the top end of the surfaces 34 and 35 are contiguous with but not in the same plane as the slot base surfaces 24 and 25.

The bracket 10A of FIGS. 4 to 6 differs from the bracket 10 of FIGS. 1 to 3 only in the form of the stops, wherein the stops, identified by the same numbers plug the suffix "a", are longer and extend beyond the edges of the bracket to provide better control. Likewise, the other embodiments will have like parts designated with the same numbers plus a suffix letter corresponding to the bracket designation legend. Further, stops 30a and 31a defining stop surfaces 34a and 35a are in the form of square-in-cross-section bars that may be made from heavy wire and soldered to the flanges of the bracket. The bars may extend to the edges of the base on which the bracket is mounted, or even beyond the edges, as illustrated.

While the purpose of the stop surfaces 34a and 35a will be more clearly described, the surface 34a functions as a stop for the archwire 23 when coacting with the underside 40d of the head of lock pin 40 during relative crown tipping between the archwire and bracket, as seen in FIG. 5, and the surface 35a functions as a stop when coacting with the underside 42a of the pin portion of the Spring Pin appliance during the relative root uprighting action, as seen in FIG. 6. Thus, stop surface 34a controls tipping in one direction, while stop surface 35a controls uprighting in the other direction. The position of the undersurfaces of the lock pin head and the Spring Pin appliance are designed to work with the angle of inclination of the respective stop, so that stop action is accomplished when the archwire is parallel against a stop surface.

The mesial and distal stops 30, 30a and 31, 31a are defined by having flat straight stop surfaces 34, 34a and 35, 35a, although the stops could be defined by the outer edges of the archwire slot base surfaces 24 and 25 and a suitably positioned tab or the like having an upper edge disposed in the same plane as the surfaces 34, 34a and 35, 35a, as shown by the tabs or posts 60 and 61 of bracket assembly 10B in the embodiment of FIG. 7, where the length of the wire extending to a tab from the bracket body would have such a stiffness as to provide the desired control between the archwire and the bracket, as accomplished by the surfaces 34, 34a and 35, 35a. The posts could have flat upper surfaces, as shown, or rounded surfaces. Further, while the surfaces terminate at the mesial and distal vertical edges of the attaching flanges, they could terminate inward of the edges or beyond those edges, as shown in FIGS. 4 to 6.

The angles of inclination or locations of the archwire stops can depend upon the specific tooth for which the bracket is designed as well as the movement function desired by the orthodontist. For example, when the bracket is mounted on a tooth that is intended to undergo considerable retraction in the mouth, the distal crown tipping stop would normally have a greater angle of inclination than when minimum retraction is desired. For a specific tooth the angle of inclination for the root uprighting stop would tend to be the same for all patients depending on the orthodontist's treatment goals, while the angle of the crown tipping stop would depend upon the amount of retraction or protraction desired for the tooth, depending on the patient's original malocclusion. More particularly, in the Begg technique, a bracket of the type illustrated where tipping movement can be accomplished between the bracket and the archwire, the desired movement of a tooth during retraction will be to tip the crown distally, then hold the crown to resist lateral displacement, and upright the root over the crown to the ideal or desired inclination. These so-called ideal inclinations may differ among orthodontists, as does beauty in the eyes of the beholder. However, common ideal or desired inclinations for each particular tooth have been proposed. The angle of inclination is measured to the distal between the vertical axis of the mouth and the long axis of the clinical crown of a tooth. For example, the common ideal angles of inclination for the upper teeth are, respectively:

5 degrees for a central,
  9 degrees for a lateral,
  11 degrees for a cuspid,
  2 degrees for a bicuspid, and
  5 degrees for a molar.

The common inclination angles for lower teeth are:

2 degrees for centrals and laterals,
  5 degrees for the cuspids, and
  2 degrees for the bicuspids and molars.

Since we are dealing with an upper cuspid for illustration purposes, the angle of inclination of the mesial root uprighting stop surface 35a is 11 degrees. Depending upon whether the bracket is designed to accomplish maximum, average or minimum retraction, the distal stop angle of inclination may vary. For maximum retraction the angle will be at least 20 degrees; for average retraction the angle will be about 12 to 13 degrees; and for minimum retraction the angle will be about 5 degrees. Thus, considering the bracket illustrated in FIGS. 4 to 6 to be designed for an upper right cuspid tooth to obtain maximum retraction, the distal stop will control crown tipping at 20 degrees as illustrated between the mouth vertical axis reference line 50 and the bracket vertical axis line 51, and the mesial stop will control root uprighting at 11 degrees.

Where the bracket is intended to move a tooth forward and provide protraction, as is often the case with second bicuspids, the crown tipping control stop will be on the mesial side, while the root uprighting control stop will be on the distal side.

In extraction cases the crown tipping control stop would usually be on the side of the bracket toward the extraction site. Conversely, the root uprighting control stop would then be on the side of the bracket away from the extraction site.

In non-extraction cases the crown tipping stop would normally be on the distal side of the bracket and the uprighting stop on the mesial. Further, the angles of the tipping stops would tend to be closer to the angles of the uprighting stops than in extraction cases because less crown tipping would occur in non-extraction cases. In some cases the angle of the tipping stop might be equal to or even less than the angle of the uprighting stop in such non-extraction cases at least for some of the teeth such as for cuspids.

To further illustrate the operation of the present invention, reference is made to FIGS. 4, 5 and 6 where a safety lock pin like that shown in U.S. Pat. No. 3,445,933 is shown in FIGS. 4 and 5 for crown tipping movement and a Spring Pin appliance is shown mounted on the bracket in FIG. 6 for applying a root uprighting force to a tooth between the bracket and the archwire. The lock pin shown in FIGS. 4 and 5 and generally designated by the numeral 40 is of the type to allow tipping of the crown distally upon the application of a suitable force on the tooth, while the Spring Pin appliance 41 shown in FIG. 6 is intended to provide a distal uprighting of the root.

The safety lock pin in FIGS. 4 and 5 locks the archwire to the bracket while permitting tipping between the archwire and bracket. It includes a head 40a, a stem 40b, a tail 40c bent over the underside of the bracket body, and the underside 40d on the head providing a surface spaced from the slot base surfaces 24 and 25. A crown tipping force may be applied through contact with a proximating tooth having a force applied to it or by any other suitable means. For example, a distal force could be applied to the mesial of the tooth to bring the distal or crown tipping stop 30a into abutting relation with the archwire, at an angle of 20 degrees, as seen in FIG. 5.

The Spring Pin appliance not only functions to apply a force between the bracket and the archwire but also to lock the archwire in place on the bracket. The particular Spring Pin appliance illustrated includes a pin portion 42 defining a head having an underside 42a functioning like underside 40d of the pin 40, and a spring portion 43. The spring portion 43 includes a tail portion 46 that may be bent over the underside of the bracket, as illustrated in FIG. 6. Thus, the Spring Pin appliance is locked in place by the bentover tail. Further, the Spring Pin appliance 40 includes an actuating arm 47 which when hooked over the archwire 23, as shown in FIG. 6, serves to activate the spring to cause uprighting movement. The actuating arm in FIG. 6 is shown in activated position and also the resulting uprighting movement of the tooth which has brought the mesial stop or root uprighting control stop 31a into engagement with the archwire 23 at an angle of 11 degrees.

Thus, the controlled retraction of a tooth is illustrated in FIG. 5 where the tooth is tipped distally until the archwire engages the crown control stop and the underside 40d of the lock pin head which prevents further tipping. Similarly, the controlled uprighting of a tooth is illustrated in FIG. 6 where the root is moved distally until the archwire engages both the root control stop 31a and the underside 42a of the spring pin which limits further uprighting. Whether the crown of the tooth is tipped or the root of the tooth is uprighted, the limits of each movement are controlled by either the mesial or distal stops so that excessive tipping or uprighting movement are prevented. Since the stops and the base of the archwire slot are not on the same plane, it is impossible for both the mesial and distal stops to function at the same time. The brackets 10 and 10B would function in the same manner as bracket 10A.

While it is preferred to mount or integrally form the limit stops on the bracket flanges or base, they could be formed on a plate which could then be secured to the lingual side of a standard bracket, as shown by the embodiments 10C and 10D in FIGS. 8 and 9. The plate then becomes part of the bracket to define an assembly that can function like the brackets 10A, 10B and 10C.

Referring to the embodiment 10C of FIG. 8, it comprises an assembly that includes a standard Begg bracket 65 suitably secured to a plate member 66. The bracket 65 is the same as the bracket 10 in FIG. 1 except that it does not include the archwire stops secured to the attaching flanges. In this assembly, the archwire stops are formed integrally with the plate 66. Accordingly, the bracket 65 has the same structural features as the bracket 10 other than the omission of the archwire stops. The plate 66 is sized larger than the width of bracket 65, and it is provided with integrally formed archwire stops 67 and 68 having respectively stop surfaces 67a and 68a which coact with the base of the archwire slot of the bracket in the same manner as the stops 60 and 61 in the embodiment 10B of FIG. 7. It will be appreciated that the plate 66 is secured to the flanges of the bracket 65 by suitable soldering or welding operations, and that the plate 65 may in turn be mounted on a bonding base for bonding the assembly to a tooth or on a band which may in turn be cemented for a tooth. The plate 66 with the stops 67 and 68 may be made by casting or any other suitable method.

The assembly 10D of FIG. 9 differs from the assembly 10C in that it includes a plate 70 that may be suitably secured to the attaching flanges of a standard bracket 65 and which would be sized to substantially correspond to the width and height of the attaching flanges. Further, the plate would be provided with tabs that can be bent over the attaching flanges to define archwire stops coacting with the archwire slot of the bracket body in the same manner that the stops 67 and 68 of the embodiment 10C coact with the archwire slot of the bracket 65. More particularly, the plate 70 may include one form of an archwire stop designated 71 which would be in the form of a tab extending from the plate member 70, and when the bracket is mounted by soldering or welding to the plate, the tab could be bent over the edge of one attaching flange and reversely bent to provide a stop surface 71a coacting with the base of the archwire slot. As an alternative type of tab member, the archwire stop 72 is in straight form and extends substantially perpendicular to the plate member 70 along the outside of the other attaching flange of the b racket 65 but also to provide a stop surface 72a that will coact with the archwire slot of the bracket. While the tab members shown extend from the mesial and distal edges of the plate 70, they could extend from the bottom edge of the plate and be bent upward. Additionally, a layer of mesh 73 may be suitably attached to the backside of the plate member 70 so that the entire assembly can be directly bonded to a tooth. It will also be appreciated that in place of the mesh 73, the plate could be suitably attached to a band for cementing to a tooth, or to a pad that could be directly bonded to a tooth.

The embodiment 10E of FIG. 10 differs from the embodiment 10B of FIG. 7 only in that a single post 75 is mounted on one of the attaching flanges of the bracket to coact with the archwire slot and in this case on the mesial flange where the bracket would be used for retraction and where only control of the uprighting movement would be desired. It is usually more important to control the uprighting movement rather than the tipping movement, and where only one stop would be used, it would be for controlling uprighting. Further, the cross section of the stop is cylindrical to illustrate form of post that would serve in substantially the same manner as the posts shown in FIG. 7.

The operation of the embodiments 10B, 10C, 10D and 10E would be the same as the previously described embodiments as to providing the desired tipping and/or uprighting control.

The present invention could likewise be incorporated in a plastic molded bracket or a metal cast bracket having a base portion radiating from a body portion where stops are formed on the base portion at one or both sides of the body portion, as shown by the bracket 10F in FIG. 11.

The embodiment 10F represents a bracket that may be molded of plastic or cast from metal wherein it includes a body portion 77 having a base portion 78 radiating from the body portion and on which archwire stops 79 and 80 are integrally formed. The archwire stops 79 and 80 are provided with stop surfaces 79a and 80a, respectively. The back surface of the base portion 78 may be suitably formed with a roughened or undercut configuration so that the bracket may be directly bonded to a tooth. This bracket would operate in the same fashion as the embodiment 10 in FIG. 1 and merely further illustrates that the archwire stops of the invention may be utilized in any type of light-wire bracket, whether it be of the type shown in FIG. 1 or whether it be molded or cast.

From the foregoing, it will be appreciated that the system of the invention with its tipping and uprighting control stops will insure the desired amounts of individual tooth tipping and uprighting while at the same time prevent undesired tipping and uprighting movements heretofore often experienced in the Begg technique.

It will be understood that modifications and variations may be effected without departing from the scope of the novel concepts of the present invention, but is is understood that this application is to be limited only by the scope of the appended claims.

The invention is hereby claimed as follows:

1. An orthodontic bracket adapted to be used for moving a tooth along an archwire including a body having connected occlusogingivally extending mesial, labial and distal walls defining an occlusogingivally extending opening and an archwire slot opening to the gingival, attaching flanges at the lingual side of the body, and archwire stop means mounted on the labial side of the attaching flanges, said stop means including a mesial archwire stop disposed on the mesial side of said body and a distal archwire stop disposed on the distal side of said body, each said stop having a gingival facing surface opposite the archwire inclined occlusally from the base of said archwire slot at a predetermined angle from the horizontal axis of the bracket, the inclination at the distal side being greater than that at the mesial side for retraction movement to permit tipping of the crown to a predetermined position from moving the tooth along the archwire, the inclination at the mesial side being equal to a predetermined angulation of the long axis of the clinical crown.

2. The orthodontic bracket of claim 1, wherein the distal angle is from 5 to 25 degrees, and the mesial angle is from 2 to 11 degrees.

3. The orthodontic bracket of claim 1, wherein for a cuspid tooth the distal angle is about 5 degrees to produce minimum retraction and the mesial angle is equal to the desired ideal inclination from the vertical of the long axis of the clinical crown when the tooth is at the desired location along the archwire.

4. The orthodontic bracket of claim 1, wherein for a cuspid tooth the distal angle is about 12 degrees to produce average retraction and the mesial angle is equal to the ideal inclination from the vertical desired of the long axis of the clinical crown when the tooth is at the desired location along the archwire.

5. The orthodontic bracket of claim 1, wherein for a cuspid tooth the distal angle is about 20 degrees to produce maximum retraction and the mesial angle is equal to the ideal inclination from the vertical of the long axis of the clinical crown when the tooth is at the desired location along the arch.

6. An orthodontic bracket for use in the Begg technique having a body with an occlusogingivally extending opening, an attaching flange at each of the mesial and distal sides of the body and along the lingual, a gingivally opening mesiodistally extending archwire slot at the gingivolingual corner of the body, and archwire stop means on the labial side of said attaching flanges, said stop means including mesial and distal archwire stops respectively on the mesial and distal sides of said body, one of said stops having a gingivally facing surface of a buccolingual width substantially that of said slot and inclined downwardly from the base of said archwire slot at an angle equal to the angle desired for the long axis of the clinical crown for a given tooth, the other of said stops having a gingivally facing surface of a buccolingual width substantially that of said slot and inclined downwardly from the base of the archwire slot at an angle greater than the angle of inclination of the other stop and depending upon the need for crown tipping for retraction or protraction of the tooth on which the bracket is to be mounted.

7. The orthodontic bracket defined in claim 6, wherein the angle of inclination of the distal stop for a given tooth of which a given amount of retraction movement is desired will be between 5 and 25 degrees for cuspid teeth.

8. The orthodontic bracket defined in claim 7, wherein the angle of inclination of the mesial stop is equal to the ideal angulation.

9. The orthodontic bracket defined in claim 6, wherein for retraction movement the distal stop controls crown tipping and the mesial stop controls root uprighting.

10. The orthodontic bracket defined in claim 6, wherein for protraction movement of a tooth the distal stop controls crown tipping and the mesial stop controls root uprighting.

* * * * *

UNITED STATES PATENT AND TRADEMARK OFFICE
CERTIFICATE OF CORRECTION

PATENT NO. : 4,664,626

DATED : May 12, 1987

INVENTOR(S) : Peter C. Kesling

It is certified that error appears in the above–identified patent and that said Letters Patent are hereby corrected as shown below:

```
Col. 1, line 56, after "cause" insert --either--;
Col. 4, line 6, after "inclination" insert a period (.)
                and change "the" to --The--;
Col. 5, line 10, after "to" insert --produce--;
        line 20, change "wtih" to --with--;
Col. 6, line 57, change "plug" to --plus--;
Col. 9, line 60, change "for" to --to--;
Col. 10, line 15, change "b racket" to --bracket--; and
         line 37, after "illustrate" insert --another--.
```

Signed and Sealed this

Twenty-fifth Day of August, 1987

Attest:

DONALD J. QUIGG

*Attesting Officer*        *Commissioner of Patents and Trademarks*